United States Patent
Furuta

(10) Patent No.: US 8,747,303 B2
(45) Date of Patent: Jun. 10, 2014

(54) METHOD FOR AFFIXING ENDOSCOPE CURVED SECTION PROTECTIVE SHEATH

(75) Inventor: Tsuyoshi Furuta, Tokyo (JP)

(73) Assignee: Hoya Corporation, Tokyo (JP)

( * ) Notice: Subject to any disclaimer, the term of this patent is extended or adjusted under 35 U.S.C. 154(b) by 76 days.

(21) Appl. No.: 13/504,332

(22) PCT Filed: Sep. 14, 2010

(86) PCT No.: PCT/JP2010/065846
§ 371 (c)(1),
(2), (4) Date: Apr. 26, 2012

(87) PCT Pub. No.: WO2011/052303
PCT Pub. Date: May 5, 2011

(65) Prior Publication Data
US 2012/0215068 A1    Aug. 23, 2012

(30) Foreign Application Priority Data
Nov. 2, 2009  (JP) ................................ 2009-252062

(51) Int. Cl.
*A61B 1/00* (2006.01)

(52) U.S. Cl.
USPC ........... 600/125; 600/121; 600/127; 600/129; 156/187

(58) Field of Classification Search
USPC ................................. 600/127, 129
See application file for complete search history.

(56) References Cited

U.S. PATENT DOCUMENTS

| | | | | |
|---|---|---|---|---|
| 4,347,837 A * | 9/1982 | Hosono | | 600/139 |
| 4,805,596 A * | 2/1989 | Hatori | | 600/139 |
| 4,807,598 A * | 2/1989 | Hasegawa | | 600/140 |
| 4,879,991 A * | 11/1989 | Ogiu | | 600/129 |
| 5,281,454 A * | 1/1994 | Hanson | | 428/36.3 |
| 5,591,120 A | 1/1997 | Machida et al. | | |
| 6,447,445 B1 * | 9/2002 | Hirano | | 600/129 |
| 6,514,198 B2 * | 2/2003 | Ishibiki | | 600/133 |
| 7,833,154 B2 * | 11/2010 | Aono et al. | | 600/140 |
| 8,226,547 B2 * | 7/2012 | Tsutsumi | | 600/140 |

FOREIGN PATENT DOCUMENTS

| | | |
|---|---|---|
| JP | 63-158302 | 10/1988 |
| JP | 6-319677 | 11/1994 |
| JP | 8-152564 | 6/1996 |
| JP | 2008-055052 | 3/2008 |
| JP | 4236305 | 12/2008 |

* cited by examiner

*Primary Examiner* — Matthew J Kasztejna
(74) *Attorney, Agent, or Firm* — Greenblum & Bernstein P.L.C.

(57) ABSTRACT

The protective sheath front end of the disclosed curved section protective sheath for covering the curved section of an endoscope covers the outer periphery of the front end of the endoscope. A filamentous member is wound around the outer periphery of the protective sheath front end, affixing the protective sheath front end to the front end of the endoscope. An adhesive agent is layered on the outer periphery of the protective sheath front end so as to cover the filamentous member. A ring member is fitted to the protective sheath front end so as to cover the adhesive agent. The inner surface of the ring member is bonded to the filamentous member with the adhesive agent therebetween.

14 Claims, 7 Drawing Sheets

METHOD FOR AFFIXING ENDOSCOPE CURVED SECTION PROTECTIVE SHEATH

BACKGROUND OF THE INVENTION

1. Field of the Invention

The present invention relates to an endoscope where an end of a curved section protective sheath is affixed to an endoscope front end or a connection pipe for connecting a curved section with a flexible section with a filamentous member, and a method for manufacturing the endoscope.

2. Description of the Related Art

In an endoscope, its curved section is provided by allowing a braided pipe to cover a curved pipe having a plurality of curved pieces connected with each other and subsequently allowing a tubular curved section protective sheath made of rubber to cover the braided pipe. In the curved section protective sheath, its front end is arranged to cover the outer periphery of the endoscope front end, while its rear end is arranged to cover a connection pipe for connecting the curved section with a flexible pipe. The front end and the rear end of the curved section protective sheath are respectively affixed to the outer periphery of the front end of the endoscope and the outer periphery of the connection pipe by a wound filament to waterproof the interior of the endoscope.

To prevent the filament from coming off, conventionally, there is known a technique of applying an adhesive agent onto a wound filament to cover it in the adhesive agent (see Patent Document No. 1). Instead of using the adhesive agent, alternatively, there is a case of either using another filament whose outer periphery is covered with thermoplastic resin (see Patent Document No. 2) or arranging an annular exterior body made of thermoplastic resin on the wound filament (see Patent Document No. 3). In common with these cases, after arranging a heat-shrinkable tube to cover the wound filament or the exterior body, heat is applied to the heat-shrinkable tube, so that the filament is covered in molten thermoplastic resin. In Patent Document Nos. 2 and 3, after being heated, the heat-shrinkable tube is detached from an end of the sheath.

Patent Document No. 1: Japanese Unexamined Patent Publication (Heisei) No. 6-319677

Patent Document No. 2: Japanese Unexamined Patent Publication No. 2008-55052

Patent Document No. 3: Japanese Patent Publication No. 4236305

SUMMARY OF THE INVENTION

Problems to be Solved by the Invention

Meanwhile, the endoscope is generally disinfected or sterilized by dipping it in chemicals etc. in everyday use. In the endoscope disclosed in the above patent documents, a filamentous member is protected from the chemicals by the adhesive agent or the thermoplastic resin. However, as the adhesive agent or the thermoplastic resin is exposed to the outer periphery of the endoscope, there is a possibility that the adhesive agent or the thermoplastic resin deteriorate prematurely due to exposure to the chemicals, causing a situation where the filamentous member is not protected sufficiently. Alternatively, there is also a possibility that such a deteriorated adhesive agent or thermoplastic resin may dissolve and remain in a human body.

Again, in the manufacturing method of Patent Document No. 1, the coating operation of the adhesive agent is apt to vary widely due to the manual labor involved, and additionally, thickness of the adhesive agent must be increased in order to improve its chemical resistance. If the adhesive agent is thickened or unevenly applied in this way, it may cause problems such as increasing the difficulty of inserting an endoscope or the like.

In the manufacturing method of Patent Document No. 2, furthermore, there is a possibility that when the thermoplastic resin on the outer periphery of the filament is molten, the filament is wound down to reduce its constriction force for affixing to the curved section protective sheath. Additionally, if air is introduced between the filament and the heat-shrinkable tube when covering the filament with the cover, air bubbles may form on the surface of the thermoplastic resin and result in a nonuniform surface condition for the thermoplastic resin. In common with Patent Documents Nos. 2 and 3, it is further noted that the heat-shrinkable tube is cut off for its removal. Thus, there is a possibility that the surface of the thermoplastic resin may be damaged when the tube is cut off.

Taking the above-mentioned problems into consideration, an object of the present invention is to provide an endoscope that can protect an adhesive agent, which is used for covering a filamentous member, by preventing the filamentous member and the adhesive agent from deteriorating, and thereby preventing the thickening of the adhesive agent so that the insertability of an endoscope can be improved.

Means of Solving the Problems

According to the present invention, there is provided an endoscope comprising: a tubular curved section protective sheath covering an endoscope curved section, the curved section protective sheath having its own end covering an outer periphery of an attachment section in the form of a pipe; a filamentous member wound around the outer periphery of the end to affix said end to said attachment section; an adhesive agent layered on the outer periphery of said end so as to cover said filamentous member; and a ring member fitted to the outer periphery of said end so as to cover said adhesive agent, said ring member having its inner peripheral surface bonded to said filamentous member with the adhesive agent.

The above attachment section is provided along an axial direction thereof from its one end side, with at least a first section, such as a small-diameter section, and a second section, such as a large-diameter section. The small-diameter section is smaller in outer diameter than the large-diameter section. It is preferable that the curved section protective sheath is adapted so as to cover the attachment section through the one end side of the attachment section, so that the end covers the outerperiphery of the first section, while the curved section envelop does not cover the outer periphery of the second section. More preferably, the ring member is arranged so as to extend the first and second sections and also bonded directly to the outer periphery of the second section through the adhesive agent.

For example, the ring member includes a small-diameter ring section and a large-diameter ring section, which is larger in inner diameter than the small-diameter ring section, and the large-diameter ring section covers the first section, while the small-diameter ring section covers the second section. Further, it is preferable that a separating distance between the filamentous member and the inner peripheral surface of the ring member is greater than a distance between the outer peripheral surface of the second section and the inner peripheral surface of the ring member. The separating distance between the filamentous member and the inner peripheral surface of the ring member is, for example, less than 0.05 mm. Additionally, the end is arranged in a concave part of the attachment section.

Preferably, the curved section protective sheath has a step section arranged in the vicinity of the end that is reduced in diameter due to constriction with the filamentous member, the step section having its outer diameter tapered gradually, and the ring member having one end arranged so as to abut against the step section. A ring member's surface in contact with the adhesive agent, at least in part, may be either a roughened surface or provided with irregularities. The attachment section is, for example, a connection pipe for connecting a front end or the curved section of an endoscope with its flexible section.

According to the present invention, there is also provided a method of manufacturing an endoscope, comprising a first step of allowing an end of a tubular curved section protective sheath for covering an endoscope curved section to cover the outer periphery of an attachment section, a second step of winding a filamentous member around the outer periphery of the end thereby to affix the end to the attachment section, a third step of layering an adhesive agent on the outer periphery of the end so as to cover the filamentous member, and a fourth step of fitting a ring member to the outer periphery of the end so as to cover the adhesive agent thereby bonding the inner peripheral surface of the ring member to the filamentous member with the adhesive agent.

Effect of the Invention

In the present invention, as the adhesive agent for protecting the filamentous member is covered with the ring member, the filamentous member and the adhesive agent are prevented from deteriorating and also part of the wound filamentous member is prevented from having its wall thickness increased.

Figure 1:
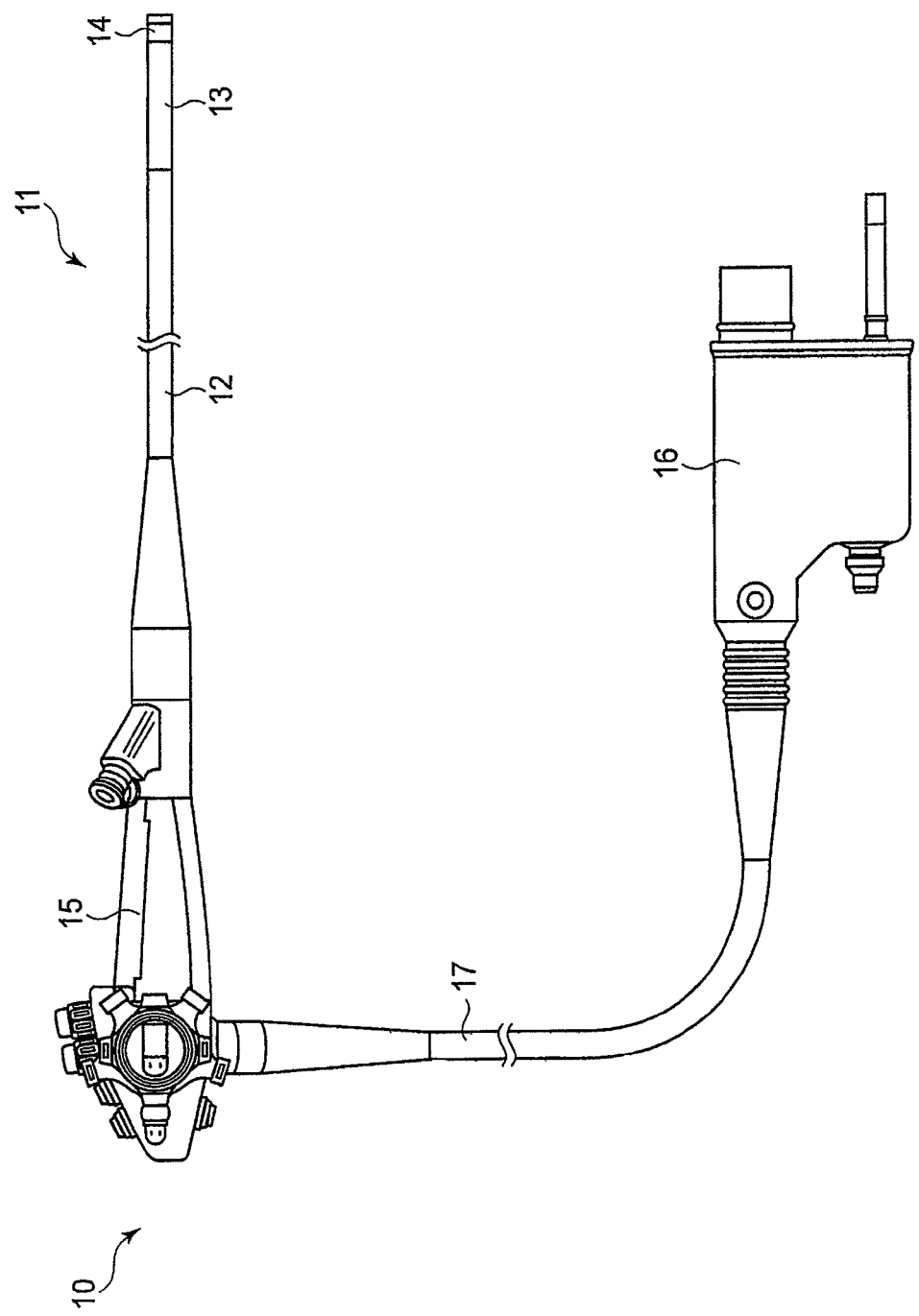
FIG. 1 is a schematic view showing an overall structure of an endoscope.

DESCRIPTION OF THE FIGURES 10 endoscope
11 insertion section
12 flexible section
13 curved section
14 front end of endoscope (attachment section)
14B large-diameter section (second section)
14C small-diameter section (first section)
14D annular groove (concave part)
23 curved section protective sheath
23A protective sheath front end
23B protective sheath rear end
23C intermediate section
23D, 23F step section
30 connection pipe (attachment section)
32, 42 filamentous member
33, 43 adhesive agent
34, 44 ring member
34A small-diameter ring section
34B large-diameter ring section

DESCRIPTION OF THE PREFERRED EMBODIMENTS

An embodiment of the present invention will be described with reference to drawings below. FIG. 1 is a schematic view of an endoscope in accordance with one embodiment of the present invention. As shown in FIG. 1, the endoscope 10 includes an insertion section 11, a manipulating section 15 grasped by a user to operate the endoscope 10, and a connector section 16 for connecting the endoscope 10 with a processor (not shown). The insertion section 11 includes a flexible section 12 with flexibility, a curved section 13 connected to a front end of the curved section 13 and an endoscope front end 14 connected to a front end of the curved section 13. The manipulating section 15 is connected to the connector section 16 through a universal cable section 17.

An image pickup device (not shown) is arranged inside the endoscope front end 14, so that an image signal of a subject obtained by the image pickup device is transmitted to the processor. Also, a light guide (not shown) is inserted into the endoscope through the connector section 16 up to the front end 14. Through the light guide, illuminating light is irradiated from the endoscope front end 14 onto the subject.

Figure 2:
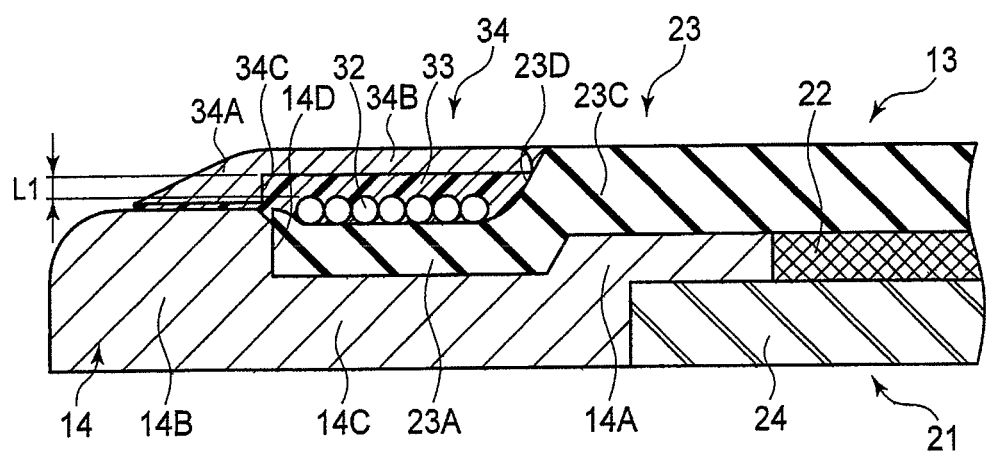
FIG. 2 is a cutaway sectional view showing a connecting structure between a front end of the endoscope and its curved section.
Figure 3:
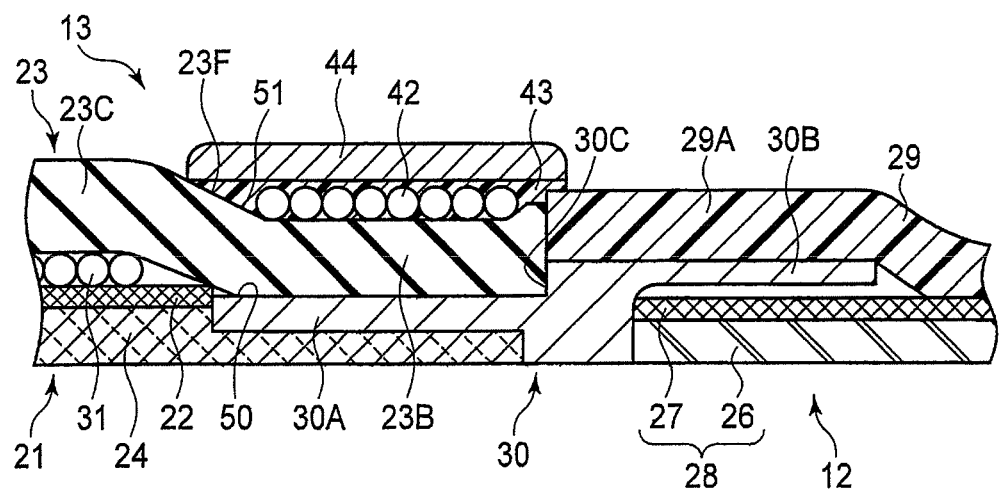
FIG. 3 is a cutaway sectional view showing a connecting structure between the curved section and a flexible section.

FIG. 2 is an enlarged sectional view showing a connecting section between the endoscope front end and the curved section. FIG. 3 is an enlarged sectional view showing a connecting section between the curved section and the flexible section. The curved section 13 comprises a curved pipe 21, a braided pipe 22 covering the outer periphery of the curved pipe 21, and a tubular curved section protective sheath 23 covering the outer periphery of the braided pipe 22 and also made of elastic material, such as rubber. The curved pipe 21 is formed of an elongated tube having a plurality of curved pieces 24 rotatably connected to each other with rivets. The curved pipe 21 is curved by remote control from the manipulating section 15 through a not-shown guide wire.

As shown in FIG. 2, the endoscope front end 14 is a tubular member, which is made from hard resin, metal or the like. The endoscope front end 14 is provided with, along its axial direction from the rear end side, a large-diameter section 14A, (i.e., an enlarged-diameter section), a small-diameter section 14C and a large-diameter section 14B. The smaller-diameter section 14C is smaller in outer diameter than the large-diameter sections 14B, 14A, so that an annular groove (annular concave part) 14D is formed on the outer peripheral side of the small-diameter section 14C. The endoscope front end 14 is connected to the curved pipe 21 by way of the large-diameter section 14A on the rear end side being fitted to the front end of the curved pipe 21 (a curved piece 24 on the foremost side).

As shown in FIG. 3, the rear end of the curved section 13 is connected to the curved flexible 12 through a connection pipe 30. The connection pipe 30 is a tubular member, which comprises a small-diameter section 30A on the front end side and a large-diameter section 30B on the rear end side, which is larger in its outer diameter that the small-diameter section 30A. The small-diameter section 30A has its outer peripheral surface connected to the outer peripheral surface of the large-diameter section 30B through a step section 30C. The rear end of the curved pipe 21 (a curved piece 24 on the rearmost side) is fitted into the small-diameter section 30A of the connection pipe 30, so that the curved section 13 is connected to the connection pipe 30.

The curved pipe 21 is covered with the braided pipe 22, and its rear end is connected to the front end of the small-diameter section 30A. The rear end of the braided pipe 22 is affixed to the outer peripheral surface of the rearmost curved piece 24 of the curved pipe 21 by a filamentous member 31 of the braided pipe, which is wound around the outer periphery of the braided pipe. The curved section protective sheath 23 covering the outer periphery of the braided pipe 22 is configured with a protective sheath front end 23A to cover a part of the endoscope front end 14 (see FIG. 2) and a protective sheath rear end 23B to cover a part of the connection pipe 30 (see FIG. 3).

The flexible section 12 comprises a tubular flexible pipe protective sheath 29 covering the outer periphery of a flexible pipe 28. The flexible pipe 28 comprises a spiral pipe 26 and a braided pipe 27 covering the outer periphery of the spiral pipe 26. The front end of the flexible pipe 28 is arranged in the large-diameter section 30B and also affixed to an interior portion of the large-diameter section 30B. The front end 29A of the flexible pipe protective sheath 29 is arranged so as to cover the large-diameter part 30B of the connection pipe 30 and furthermore, an inner peripheral surface of the front end is bonded to the outer peripheral surface of the large-diameter section 30B.

Next, a structure where the front end (protective sheath front end) 23A of the curved section protective sheath 23 is affixed to the endoscope front end 14 will be described with reference to FIG. 2, in detail. As shown in FIG. 2, the curved section protective sheath 23 covers the endoscope front end 14 from the rear end side up to the small-diameter section 14C, so that the protective sheath front end 23A is arranged in the annular groove 14D. It should be noted that, the curved section protective sheath 23 is not arranged so as to cover the large-diameter section 14B of the endoscope front end 14.

The protective sheath front end 23A arranged in the annular groove 14D is affixed to the endoscope front end 14 by a filamentous member 32 wound around the outer periphery of the protective sheath front end. An adhesive agent 33 is layered on the outer periphery of the protective sheath front end 23A so as to cover the filamentous member 32, and additionally, a ring member 34 is fitted to the outer periphery of the protective sheath front end so as to cover the adhesive agent 33. The adhesive agent 33 covers the filamentous member 32 to protect it, and also bonds the ring member 34 to the filamentous member 32 to prevent the ring member 34 from detaching from the protective sheath front end 23A.

The protective sheath front end 23A is arranged in the annular groove 14D and also constricted by the filamentous member 32 to reduce the diameter of the front end. Namely, the outer diameter of the protective sheath front end 23A is smaller than the original (inherent) diameter of the curved section protective sheath. More specifically, a step section 23D with a gradually tapered outer diameter is formed in the vicinity of the protective sheath front end 23A. For convenience sake, a part of the curved section protective sheath 23 whose outer diameter is not reduced due to the absence of externally applied pressure will be referred to as the "intermediate section 23C" in the following explanation.

Metals such as stainless steel, or resins such as polyphenylene oxide, polyetherimide (ULTEM) and polyphenysulfone, can be used in the construction of the ring member 34. As these resins are superior in biocompatibility, chemical resistance, workability and strength, they can be utilized in the construction of the ring member. Preferably, the ring member 34 is made from metal since it can be processed thinly and still retain its high strength. Adhesive agents having biocompatibility and high chemical resistance, such as epoxy resin, are available for the adhesive agent 33.

Figure 4:
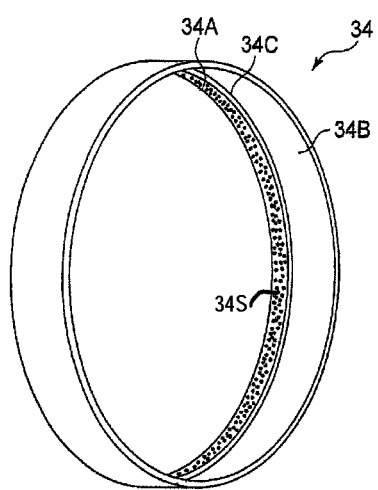
FIG. 4 is an enlarged perspective view showing the structure of a ring member.

As shown in FIG. 4, the ring member 34 is shaped in the form of a thin generally-circular ring and also composed of a small-diameter ring section 34A on the front end side and a large-diameter ring section 34B on the rear end side, which is larger in inner diameter than the small-diameter ring section 34A. The inner peripheral surface of the small-diameter ring section 34A is connected to the inner peripheral surface of the large-diameter ring section 34B through a step section 34C. The inner diameters of the small-diameter ring section 34A and the large-diameter ring section 34B are constant respectively. The outer diameter of the small-diameter ring section 34A decreases with respect to the decreasing distance from the front end. In other words, the outer peripheral surface of the small-diameter ring section 34A is formed in a tapered shape. With the adoption of such a configuration, the invention guarantees improved operability of an endoscope and a reduction in the amount of time the endoscope front end 14 needs to be inserted inside of a body cavity of a patient undergoing diagnostic testing. Meanwhile, the outer diameter of the large-diameter ring section 34B is constant.

As shown in FIG. 2, the ring member 34 is arranged so as to extend the large-diameter section 14B and the small-diameter section 14C of the endoscope front end 14. Concretely, the large-diameter ring section 34B is arranged outside the protective sheath front end 23A so as to cover the filamentous member 32 while also being adhered to the filamentous member 32 through the adhesive agent 33. The small-diameter ring section 34A is arranged so as to fit the outer periphery of the large-diameter section 14B of the endoscope front end 14.

The adhesive agent 33 layered on the outer periphery of the protective sheath front end 23A is arranged so as to partially protrude between the small-diameter ring section 34A and the large-diameter section 14B, allowing the small-diameter ring section 34A to adhere to the outer peripheral surface of the large-diameter section 14B. Additionally, the adhesive agent 33 is arranged so as to also protrude between a rear end surface of the large-diameter ring section 34B and the step section 23D. Consequently, the rear end surface of the large-diameter ring section 34B abuts against the step section 23D through the adhesive agent 33 and thus adheres to the step section 23D via the adhesive agent 33. Preferably, the rear end surface of the large-diameter ring section 34B is adhesively joined to the step section 23D while being pressed against it. Consequently, due to the elasticity of the step section 23D, the above rear end surface and the step section 23D are held substantially tightly together, so that improved airtightness of the endoscope front end 14 is ensured.

As the protective sheath front end 23A is smaller in outer diameter than the intermediate section 23C, there is a step between the outer peripheral surfaces of the former and the latter. According to this embodiment, the step is eliminated by the filamentous member 32, the adhesive agent 33 and the ring member 34, so that the outer peripheral surface of the ring member 34 is in the same plane as the outer peripheral surface of the intermediate section 23C. Namely, the outer diameter of the large-diameter ring section 34B is equalized to the outer diameter of the intermediate section 23C of the curved section protective sheath 23.

The inner peripheral surface of the large-diameter ring section 34B is arranged so as to depart from the filamentous member 32. It is desirable that a separating distance (clearance) L1 between the inner peripheral surface of the large-diameter ring section 34B and the filamentous member 32 is greater than the a distance between the innerperipheral surface of the small-diameter ring section 34A and the outer peripheral surface of the large-diameter section 14B, but less than 0.05 mm. As the filamentous member 32 is separated from the large-diameter ring section 34B, the adhesive agent 33 layered therebetween prevents the filamentous member from coming into contact with the ring member 34. Additionally, due to the adhesive agent therebetween, the filamentous member 33 is completely covered in the adhesive agent 33 and also sufficiently protected by the adhesive agent. Further, by making the clearance L1 less than 0.05 mm, it prevents the ring member 34 from being eccentrically moved in a later-mentioned adhesive wiping process etc.

The inner peripheral surface of the small-diameter ring section 34A is arranged so as to extend along the outer peripheral surface of the large-diameter section 14B of the endoscope front end 14. The inner diameter of the small-diameter ring section 34A is generally equal to the outer diameter of the large-diameter section 14B. Also by such a configuration, the ring member 34 is prevented from being eccentrically displaced in the later-mentioned adhesive wiping process, etc.

Next, a structure where the rear end (protective sheath rear end) 23B of the curved section protective sheath 23 is affixed to the connection pipe 30 will be described with reference to FIG. 3. Note, constitutions unmentioned in the following description especially, for example, respective materials of the filamentous member, the adhesive agent and the ring member, are the same as those of the structure where the protective sheath front end 23A is affixed to the endoscope front end 14.

As shown in FIG. 3, the curved section protective sheath 23 covers the connection pipe 30 from the front end side of the connection pipe 30, so that the protective sheath rear end 23B covers the small-diameter section 30A of the connection pipe 30. Meanwhile, the large-diameter section 30B of the connection pipe 30 is not covered by the curved section protective sheath 23 but instead covered by the flexible section protective sheath 29 as mentioned above. The rear end surface of the protective sheath rear end 23B is abuts on the respective front end surfaces of the step section 30C and the flexible pipe protective sheath 29. The protective sheath rear end 23B is affixed to the small-diameter section 30A by a filamentous member 42 wound around the outer periphery of the protective sheath rear end.

The small-diameter section 30A is smaller in diameter than its anteroposterior sections (the filamentous member 31 for the braided pipe and the large-diameter section 30B) to provide on its outer peripheral side an annular concave part 50 in which the protective sheath rear end 23B is arranged. Then, the protective sheath rear end 23B is constricted by the filamentous member 42 and thus reduced in diameter to have a relatively smaller diameter in comparison to its anteroposterior protective sheath (i.e. the intermediate section 23C of the curved sect ion protective sheath 23 covering the filamentous member 31 for the braided pipe, and the front end 29A of the flexible pipe protective sheath 29). Consequently, the outer peripheral side of the protective sheath rear end 23B becomes indented relative to the outer peripheral surfaces of the anteroposterior protective sheath sections, forming an annular concave part 51. Note, the outer peripheral surface of the protective sheath rear end 23B is connected to the intermediate section 23C through a tapered step section 23F forming a sidewall of the annular concave part 51.

The interior of the annular concave part 51 (that is, the outer peripheral side of the protective sheath rear end 23B) is filled with the adhesive agent 43 in which the filamentous member 42 is covered. Further, on the outer peripheral side of the protective sheath rear end 23B, a ring member 44 is fitted to it so as to enclose the annular concave part 51 and cover the adhesive agent 43.

The ring member 44 is shaped to be a thin-walled circular ring having constant inner and outer diameters, respectively. The ring member 44 is adhesively affixed to the filamentous member 42 and the outer peripheral surface of the protective sheath rear end 23B through the adhesive agent 43 filling the annular concave part 51. Note, as the interior of the concave part accommodating the filamentous member 42 therein is filled with the adhesive agent, the filamentous member 42 is completely covered in the adhesive agent. Consequently, the filamentous member 42 is prevented from coming into contact with the inner peripheral surface of the ring member 44.

The adhesive agent 43 filling the annular concave part 51 also occupies the space between the front end of the ring member 44 and the step section 23F. Namely, the front end of the ring member 44 abuts on the step section 23F through the adhesive agent 43 and is bonded to the step section 23F with the adhesive agent 43. The rear end of the ring member 44 is arranged on the outer peripheral side of the front end 29A of the flexible section protective sheath 29. The adhesive agent 43 in the annular concave part 51 partially covers the outer periphery of the front end 29A, so that the rear end of the ring member 44 is also bonded to the front end 29A with the adhesive agent 43.

Figure 5:
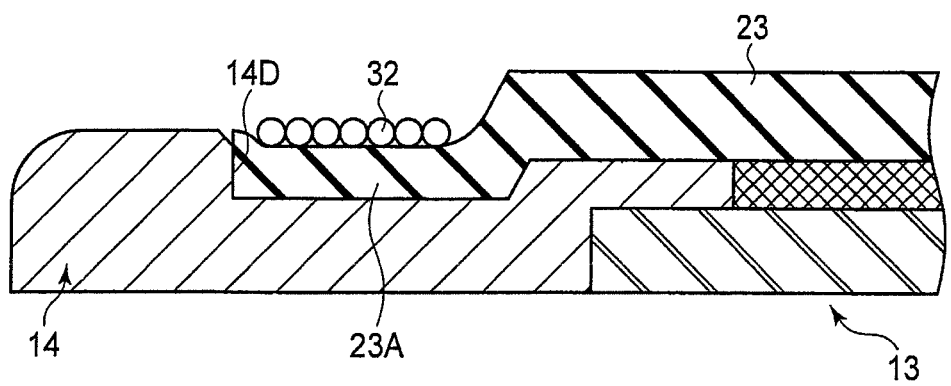
FIG. 5 is a cutaway sectional view to show a manufacturing method of the endoscope.

Next, a method of manufacturing the endoscope in accordance with an embodiment of the present invention will be described with reference to FIGS. 5 to 7. First, as shown in FIG. 5, the manufacturing method is designed to allow the curved section protective sheath 23 to cover the curved sect ion 13 and a part of the endoscope front end 14 to fit the protective sheath front end 23A in the annular groove 14D of the protective sheath front end 14. Next, the filamentous member 32 is wound around the outer periphery of the protective sheath front end 23A with plural windings, thereby affixing the protective sheath front end 23A to the endoscope front end 14.

Figure 6:
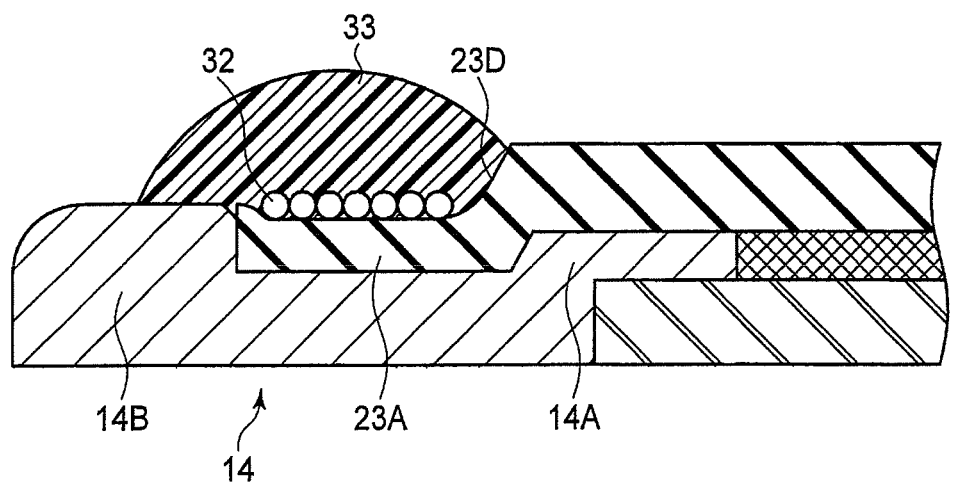
FIG. 6 is a cutaway sectional view to show a manufacturing method of the endoscope.

Next, as shown in FIG. 6, the adhesive agent 33 in the form of a liquid or fluid is applied to the outer peripheral surface of the protective sheath front end 23A from the outer side of the filamentous member 32. The adhesive agent 33 is applied so as to cover the large-diameter section 14B of the endoscope front end 14, the protective sheath front end 23A and also the step section 23D.

Next, before the adhesive agent 33 becomes hardened or solidified, the ring member 34 is attached on the outer periphery of the large-diameter section 14B of the endoscope front end 14 and subsequently, the ring member 34 is shifted backward until it abuts on the step sect ion 23D. Consequently, the ring member 34 is fitted to the outer periphery of the protective sheath front end 23A, as shown in FIG. 7.

The volume of the adhesive agent 33 applied between the ring member 23 and the endoscope front end 14 is greater than the clearance space. Thus, when the ring member 34 is fitted, the clearance between the ring member 34 and the endoscope front end 14 is completely filled with the adhesive agent, leaving no air bubbles inside the ring member 34.

Thus, the adhesive agent 33 completely fills the clearance between the large-diameter ring section 34B and the protective sheath front end 23A to bond the large-diameter ring section 34B to the filamentous member 32 and the outer peripheral surface of the protective sheath front end 23A. The adhesive agent is further applied between the small-diameter ring section 34A and the large-diameter section 14B to bond the small-diameter ring section 34A to the large-diameter section 14B. The adhesive agent 33 is further applied between the rear end surface of the large-diameter ring section 34B and the step section 23D to bond the rear end of the large-diameter ring section 34B to the step section 23D.

Figure 7:
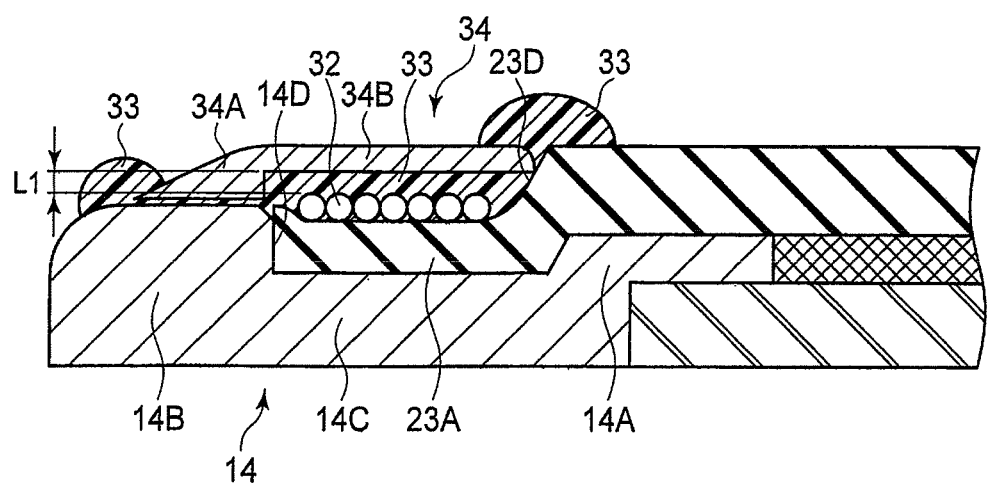
FIG. 7 is a cutaway sectional view to show a manufacturing method of the endoscope.

When fitting the ring member 34, the adhesive agent 33 partially protrudes outside the ring member 34, as shown in FIG. 7. The extra adhesive agent 33 protruding outside is wiped away before it becomes hardened or solidified. Subsequently, the adhesive agent 33 is heated and dried, etc., to become hardened or solidified, so that the endoscope as shown in FIG. 2, is completed.

As the method for affixing the protective sheath rear end 23b to the connection pipe and additionally for fitting the ring member 44 is similar to the above-mentioned method, the description has been eliminated. However, before covering the curved section 13 with the curved section protective sheath 23, the ring member 44 is attached to the outer periphery of the flexible section 12 and so that the ring member 44 is positioned behind the connection pipe 30. Then, after applying the adhesive agent, the ring member 44 in moved forward until the ring member front end abuts on the step section 23FD, allowing the ring member 44 to fit against the outer periphery of the protective sheath rear end 23B. Such an operation is necessary because it would be difficult to fit the ring member 44 by moving it from the front side since the curved section 13 covered by the curved section protective sheath 23 is formed with a section having an outer diameter that is larger than the inner diameter of the ring member 44 (i.e. the intermediate section 44).

According to this embodiment, as mentioned above, since the adhesive agents 33, 43 used for protectively covering the filamentous members 32, 42 are covered by the ring members 33, 44 and seldom-exposed to the outer periphery of the endoscope, the adhesive agents 33, 43 are protected against deterioration caused by exposure to chemicals. Accordingly, without increasing the respective thickness of the adhesive agents 33, 43, the durability of an endoscope can be maintained appropriately, and additionally, the adhesive agents 33, 43 can be prevented from coming off.

In the manufacturing process of the endoscope, additionally, even if the adhesive agents are not applied uniformly, the adhesive agents inside the ring members 33, 34 would be uniform at the time of fitting the ring members 33, 44, and therefore, it is possible to improve the workability in manufacturing an endoscope and its yield.

Additionally, when fitting the ring members 34 and 44 to the ends 23A and 23B, an operator has only to move the ring members until they abut against the step sections 23D and 23F, respectively. Therefore, without adjusting the attaching positions, it is possible to arrange the ring members 33, 44 in their fixed positions without any adjustment to their attached positions. Additionally, as the ring member 33 fitted to the protective sheath front end 23A is provided with the small-diameter ring section 34A to be fitted to the endoscope front end 14, it is possible to affix the ring member to the outer periphery of the protective sheath front end 23A with greater stability.

Note, the inner peripheral surfaces of the ring members 34, 44 may be either rough-surfaced or provided with irregularities by means of screw cutting, etc. In the large-diameter section 14B, alternatively, the portion of its outer peripheral surface covered with the small-diameter ring section 34A may be formed with a rough surface. Namely, respective surfaces of the ring members 34, 44 and the endoscope front end 14, etc, may be rough-surfaced or provided with irregularities 34S, as shown in FIG. 4. If such a constitution is adopted, then it is possible to enhance the adhesive forces of the adhesive agents 33, 43 acting on the ring members 34, 44, owing to their anchor effects.

The invention claimed is:

1. An endoscope comprising:
    an attachment section having at least first and second sections extending in an axial direction from a rear end of said attachment section, wherein said attachment section is in the form of a pipe;
    a tubular curved section protective sheath having an end that covers an outer periphery of said first section, which extends from said rear end of said attachment section, so as to cover an endoscope curved section while leaving an outer periphery of said second section uncovered;
    a filamentous member wound around the outer periphery of said end of said tubular curved section protective sheath thereby affixing said end of said tubular curved section protective sheath to said first section of said attachment section;
    an adhesive agent layered on the outer periphery of at least said end of said tubular curved section protective sheath so as to cover said filamentous member; and
    a ring member fitted to the outer periphery of said end of said tubular curved section protective sheath so as to cover said adhesive agent, and an inner peripheral surface of said ring member being bonded to said filamentous member with said adhesive agent, wherein
    said ring member includes a small-diameter ring section having an inner diameter and a large-diameter ring section having an inner diameter, wherein said inner diameter of said large-diameter ring section is larger than said inner diameter of said small-diameter ring section,
    said large-diameter ring section is arranged surrounding said end of said tubular curved section protective sheath so as to cover said filamentous member, and
    said small-diameter ring section covers said second section and is directly bonded to said second section through said adhesive agent.

2. The endoscope according to claim 1, wherein said second section is a large-diameter section having an outer diameter and said first section is a small-diameter section having an outer diameter, wherein said outer diameter of said small-diameter section is smaller than said outer diameter of said large-diameter section.

3. The endoscope according to claim 2, wherein
    said attachment section is further provided, closer in the axial direction to said rear end of said attachment section than said smaller-diameter section, with an enlarged-diameter section that has a larger outer diameter than said outer diameter of said small-diameter section, forming a concave part on the outer peripheral side of said small-diameter section, and
    said end of said tubular curved section protective sheath is arranged in said concave part.

4. The endoscope according to claim 1, wherein a separating distance between said filamentous member and the inner peripheral surface of said ring member is larger than a distance between the outer peripheral surface of said second section and the inner peripheral surface of said ring member.

5. The endoscope according to claim 4, wherein the separating distance between said filamentous member and the inner peripheral surface of said ring member is less than 0.05 mm.

6. The endoscope according to claim 1, wherein
    said curved section protective sheath has a step section arranged in the vicinity of said end of said tubular curved section protective sheath which is reduced in diameter due to constriction with said filamentous member, said step section having an outer diameter that is gradually tapered, and said ring member has one end arranged so as to abut against the step section.

7. The endoscope according to claim 6, wherein the adhesive agent layered on the outer periphery of said end of said tubular curved section protective sheath is arranged so as to protrude between one end of said ring member and said step section to bond said end of said ring member to said step section.

8. The endoscope according to claim 1, wherein a surface of said ring member that is in contact with said adhesive agent, at least in part, is either rough-surfaced or provided with irregularities.

9. The endoscope according to claim 1, wherein said attachment section is a connection pipe that connects an endoscope front end to said endoscope curved section.

10. The endoscope according to claim 1, wherein the inner peripheral surface of said small-diameter ring section is provided along the outer peripheral surface of said second section.

11. The endoscope according to claim 1, wherein the outer peripheral surface of said small-diameter ring section is tapered.

12. The endoscope according to claim 1, wherein the adhesive agent layered on the outer periphery of said end of said tubular curved section protective sheath is arranged so as to protrude between said small-diameter ring section and said second section to bond said small-diameter ring section to said second section.

13. The endoscope according to claim 1, wherein said first and second sections are continuous with each other.

14. A method of manufacturing an endoscope, comprising:

providing an end of a tubular curved section protective sheath for covering an endoscope curved section and to cover the outer periphery of an attachment section, said attachment section having at least first and second sections extending in an axial direction from a rear end of said attachment section, wherein said attachment section is provided in the form of a pipe;

winding a filamentous member around the outer periphery of said end of said tubular curved section protective sheath thereby affixing said end of said tubular curved section protective sheath to said first section of said attachment section;

layering an adhesive agent on at least the outer periphery of said end of said tubular curved section protective sheath so as to cover said filamentous member; and fitting a ring member to the outer periphery of said end of said tubular curved section protective sheath so as to cover said adhesive agent thereby bonding the inner peripheral surface of said ring member to said filamentous member with said adhesive agent, wherein said ring member includes a small-diameter ring section having an inner diameter and a large-diameter ring section having an inner diameter, wherein said inner diameter of the large-diameter ring section is larger than said inner diameter of said small-diameter ring section, said large-diameter ring section is arranged surrounding said end of said tubular curved section protective sheath so as to cover said filamentous member, and said small-diameter ring section covers said second section and is directly bonded to said second section through said adhesive agent.

* * * * *